US006232305B1

(12) United States Patent
Singh et al.

(10) Patent No.: US 6,232,305 B1
(45) Date of Patent: May 15, 2001

(54) SUBSTITUTED AMINO BICYCLIC-β-LACTAM PENAM AND CEPHAM DERIVATIVES AS CYSTEINE PROTEASE INHIBITORS

(75) Inventors: Rajeshwar Singh; Nian Zhou, both of Edmonton (CA); Deqi Guo, Phoenixville, PA (US); Ronald G. Micetich, Sherwood Park (CA)

(73) Assignee: Naeja Pharmaceutical Inc., Alberta (CA)

( * ) Notice: Subject to any disclaimer, the term of this patent is extended or adjusted under 35 U.S.C. 154(b) by 0 days.

(21) Appl. No.: 09/010,993

(22) Filed: Jan. 22, 1998

Related U.S. Application Data
(60) Provisional application No. 60/035,885, filed on Jan. 23, 1997.

(51) Int. Cl.[7] .................... C07D 499/40; C07D 499/897; C07D 501/14; A61K 31/546; A61P 31/04
(52) U.S. Cl. .................... 514/192; 514/196; 514/197; 540/215; 540/222; 540/228; 540/230; 540/304; 540/311
(58) Field of Search .................... 540/304, 311; 514/196, 197, 192

(56) References Cited

U.S. PATENT DOCUMENTS
3,311,609 * 3/1967 Cheney ................. 540/304

FOREIGN PATENT DOCUMENTS
| | | |
|---|---|---|
| 61M | 1/1961 | (FR) . |
| 958824 * | 5/1964 | (GB) .................... 540/311 |
| 1157586 | 7/1967 | (GB) . |
| 1157586 | 7/1969 | (GB) . |
| WO 96/32408 | 10/1996 | (WO) . |
| WO/97/38008 | 10/1997 | (WO) . |

OTHER PUBLICATIONS
Otto, Chemical Reviews 97, 133–171, 1977.*
Thomas, Biochimica et Biophysica Acta 990, 246–253, 1989.*
Chemical Abstract, vol. 73, No. 7, Aug. 17, 1970; Abstract No. 35363 Hagitani A. et al.: "Penicillins".
Toya Brewing Co. Chemical Abstracts 71:91878x, vol. 71, 1969, p. 442.
Hagitani Chemical Abstracts 73:35363, vol. 73, 1970, p. 329.
Aldrich Catalog, p. 897, 1998.*
Sigma Catlog, p. 796, 1998.*

* cited by examiner

Primary Examiner—Mark L. Berch
(74) Attorney, Agent, or Firm—Arent Fox Kintner Plotkin Kahn

(57) ABSTRACT

The present invention provides substituted amino bicyclic-β-lactam penam derivatives and substituted amino bicyclic-β-lactam cepham derivatives and their diastereoisomers of formula I, as well as compositions, methods of making, and methods of using, which exhibit excellent cysteine protease inhibitory activity and which may be used for treatment of different diseases such as cancer (including cancer metastasis), osteoporosis, rheumatoid arthritis. muscular dystrophy, myocardial infarction, pulmonary emphysema, septic shock, cerebral ischemia, decreased memory function, Alzheimer, cataract, malaria, glomerular basement membrane degradation, bacterial infection, inflammatory diseases, parasitic infections and viral infections,

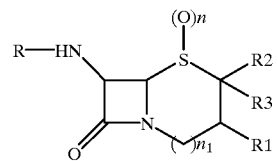

(I)

wherein

R is a peptidyl residue of a single natural α-amino acid selected from a specific group of natural α-amino acids or a peptidyl residue of a single non-natural amino acid selected from a specified group of non-natural amino acids, in which natural or non-natural peptidyl residue the terminal —$NH_2$ group is unsubstituted or substituted once or twice with group $R_4$, wherein $R_4$ is selected from the group consisting of —$COOR_5$, —$COR_5$, —$SO_2R_5$, and —$COR_6$, $R_6$ is an amino group which is unsubstituted or substituted at least once with a $C_1$–$C_6$ alkyl group which is unsubstituted or substituted, $R_1$ is selected from the group consisting of hydrogen, hydroxy, carboxy, —$COOR_6$, —$OR_7$, —$CONHR_7$, and $C_1$–$C_5$ alkyl, in which the $C_1$–$C_6$ alkyl is unsubstituted or substituted, $R_2$ and $R_3$ are independently hydrogen or $C_1$–$C_3$ alkyl which is unsubstituted or substituted, n is 0, 1, or 2, and $n_1$ is 0 or 1.

16 Claims, No Drawings

SUBSTITUTED AMINO BICYCLIC-β-LACTAM PENAM AND CEPHAM DERIVATIVES AS CYSTEINE PROTEASE INHIBITORS

This application claims priority of United States Provisional patent application Serial No. 60/035,885, filed Jan. 23, 1997.

BACKGROUND OF INVENTION

Cysteine proteases, such as cathepsins B, H, K, L, S, and $O_2$, containing a highly reactive cysteine residue with a free thiol group at the active site have been known as playing an important role in certain conditions distinguished by aberrant protein turnover such as: muscular dystrophy (Am. J. Pathol. 1986, 122, 193–198; Am. J. Pathol. 1987, 127, 461–466), myocardial infarction (J. Am. Coll. Cardiol. 1983, 2, 681–688), bone resorption (Biochem. J. 1991, 279, 167–274; J. Biol. Chem. 1996, 271, 2126–2132; and Biochem. Biophys. Acta 1992,1116, 57–66), arthritis (Arthritis Rheumatism 1994, 37, 236–247; and Biochem. Pharmacol. 1992, 44, 1201–1207),cancer, including cancer metastasis (Cancer Metastasis Rev. 1990, 9, 333–352), pulmonary emphysema (Am. Rev. Respir. Dis. 1975, 111, 579–586), septic shock (Immunol. Today 1991, 11, 404–410, Biochemistry 1994, 33, 3934–3940), cerebral ischemia, memory function, Alzheimer and cataract (TIPS 1994, 15, 412–419, Bioorg. Med. Chem. Lett. 1995 4, 387–392, Proc, Natl. Acad. Sci. USA 1991, 88,10998–11002), malaria (J. Med. Chem. 1995, 38, 5031–5037), glomerular basement membrane degradation (Biochem. Bioph. Acta 1989, 990, 246–251), bacterial infection (Nature 1989, 337, 385–386), inflammatory diseases (Protein Science 1995, 4, 3–12), parasitic infections (Annu. Rev. Microbiol. 1993, 47, 821–853; Parasitol. Today 1990, 6, 270–275), and viral infections (Biochem. 1992, 31, 7862–7869).

A variety of cysteine proteinase have been shown to be present in mammalian tissue. The most notable of these proteinase are the lysosomal cathepsins (cathepsin B, H, S, K and L) and the cytoplasmic $Ca^{2+}$ dependent enzymes, the calpains. These enzymes are, therefore, excellent targets for the development of specific inhibitors as possible therapeutic agents.

Several types of cysteine proteases inhibitors have been reported, such as peptide aldehydes (Biochim. Biophys. Acta 1991, 107–343), nitriles (Biochim. Biophys. Acta 1990, 1035, 62–70), halomethyl ketones (Anal. Biochem. 1985, 149, 461–465; Acta. Biol. Med. Ger. 1981, 40, 1503–1511; Biochem. Phar. 1992, 44, 1201–1207), diazomethyl ketones (Biochem. J. 1988, 253, 751), acyloxy methyl ketones (J. Med. Chem. 1994, 37, 1833–1840; J. Am. Chem. Soc. 1988,110, 4429–4431), ketomethylsulfonium salt (J. Biol. Chem. 1988, 263, 2768–2772), α-ketocarbonyl compounds (J. Med. Chem. 1993, 36, 3472–3480; 1994, 37, 2918–2929), vinyl sulfones (J. Med. Chem. 1995, 38, 3193–3196) and epoxysuccinyl derivatives (Agric. Biol. Chem. 1978, 42, 523–527). These inhibitors, in general, have a peptidyl affinity group and a group reactive towards the thiol of the cysteine residue in cysteine proteases.

In continuation of our efforts to find low molecular weight cysteine protease inhibitors for therapeutic uses, we have focused our attention at substituted penam and cepham derivatives of which β-lactam ring is susceptible towards acylation of cysteine proteases.

SUMMARY OF THE INVENTION

The present invention is based on the discovery that certain substituted amino bicyclic-β-lactam penam derivatives and substituted amino bicyclic-β-lactam cepham derivatives exhibit excellent cysteine protease inhibitory activity which might be used for treatment of different diseases and/or conditions such as cancer (including cancer metastasis), osteoporosis, rheumatoid arthritis. muscular dystrophy, myocardial infarction, pulmonary emphysema, septic shock, cerebral ischemia, decreased memory function, Alzheimer, cataract, malaria, glomerular basement membrane degradation, bacterial infection, inflammatory diseases, parasitic infections and viral infections. Particularly important aspects of the present invention are the use of the compounds and compositions disclosed herein in the treatment of cancer, including cancer metastasis, and in the treatment of rheumatoid arthritis.

Our laboratory has been actively involved in the search for novel types of cysteine proteases inhibitors with high selectivity among the cysteine protease class of enzymes. We have found that 3,4-disubstituted azetidinone, 2-substituted oxapenam, 6-substituted oxapenam derivatives exhibit good cysteine protease inhibitory activity. Related to the present invention are inventions disclosed in U.S. patent application Ser. Nos. 08/925,459 (pending), and 08/935,259 (pending), the entire disclosures of which are hereby.

Further to optimize and enhance activity, we have designed, synthesized and evaluated the cysteine protease inhibitory activity of various substituted amino bicyclic-β-lactam penam derivatives and substituted amino bicyclic-β-lactam cepham derivatives and the findings are reported in the present invention.

In accordance with the present invention, there are provided substituted amino bicyclic-β-lactam penam derivatives and substituted amino bicyclic-β-lactam cepham derivatives of general formula I or pharmaceutically acceptable salts thereof, (I)

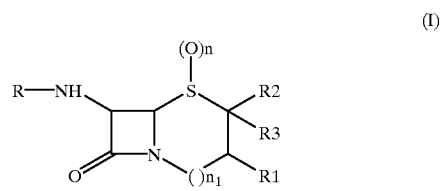

wherein
R is (a) a peptidyl residue of a single natural α-amino acid in either the L- or D-form, selected from the group consisting of D- or L-glycine, D- or L-alanine, D- or L-valine, D- or L-leucine, D- or L-isoleucine, D- or L-serine, D- or L-threonine, D- or L-aspartic acid, D- or L-glutamic acid, D- or L-asparagine, D- or L-glutamine, D- or L-lysine, D- or L-arginine, D- or L-phenylalanine, D- or L-tyrosine, D- or L-tryptophan, D- or L-histidine, D- or L-methionine, D- or L-proline, or (b) a peptidyl residue of a single non-natural amino acid in either the L- or D- form, selected from D- or L-t-butyl alanine, D- or L-homophenyl alanine, D- or L-pyridyl alanine, D- or L-thienyl alanine, D- or L-naphthyl alanine, D- or L-methoxy phenylalanine, D- or L-halophenyl alanine, D- or L-e-nitro arginine, D- or L-citrulline, D- or L-indoline carboxylic acid, D- or L-cycloalkyl glycine (e.g., cyclopentyl glycine), D- or L-cycloalkyl alanine (e.g., cyclohexyl alanine), D- or L4-hydroxy-3-nitro-phenylalanine, D- or L4-amino-3,5-diiodophenyl alanine, D- or L4-hydroxy-3,5-diiodophenyl alanine, D- or L4-hydroxy-3,5-dibromophenyl alanine, D- or L-β-(3-benzothienyl) alanine, D- or L-3,4-dihydroxy-phenyl alanine, D- or L-3,4 (methylenedioxy)phenyl alanine, D- or L-3,4 (ethylenedioxy)phenyl alanine, D- or L-4,4'-biphenyl alanine, D- or L-3,4-dichlorophenyl alanine, D- or L-iodophenyl alanine, D- or L-4-nitrophenyl alanine, D- or L-pentafluorophenyl alanine, D- or L-trifluorophenyl alanine, D- or L-thiazolyl alanine, D- or L-trifluoromethylphenyl alanine, D- or L-sulfamoyl alanine, D- or L-t-butyloxy alanine, D- or L-1-t-butyloxymethylalanine, D- or L-trimethyl alanine, D- or L-3,4-diisopropyloxyphenyl alanine, D- or L-propylalanine, and D- or L-ethylalanine, in which peptidyl residue (a) or (b) the terminal —$NH_2$ group is unsubstituted or substituted once or twice with $R_4$, wherein $R_4$ is —$COOR_5$, —$COR_5$, —$SO_2R_5$, or —$COR_6$, wherein $R_5$ is (i) a $C_1$–$C_6$ alkyl group, (ii) a $C_2$–$C_6$ alkenyl group, (iii) a $C_2$–$C_6$ alkynyl group, (iv) a $C_3$–$C_6$ cycloalkyl group, (v) a phenyl group, (vi) a naphthyl group, or (vii) a monocyclic or bicyclic heterocyclic group, which group (i), (ii), (iii), (iv), (v), (vi), or (vii) is unsubstituted or substituted by 1, 2 or 3 substituents independently selected from the group consisting of hydroxy, halogen, carboxy, $C_1$–$C_4$ alkyl (which is unsubstituted or substituted at least once with carboxy and/or amino), $C_1$–$C_2$ alkoxy, amino, cyano, phenyl and monocyclic or bicyclic heterocyclic groups, (which phenyl and monocyclic or bicyclic heterocyclic groups are unsubstituted or substituted by 1 or 2 substituents independently selected from hydroxy, halogen, carboxy, $C_1$–$C_4$ alkyl, $C_1$–$C_2$ alkoxy, amino, and cyano);

and $R_6$ is an amino group which is unsubstituted or substituted at least once with a $C_1$–$C_6$ alkyl group which is unsubstituted or substituted by 1 or 2 substitutents selected from the group consisting of hydroxy, halogen, cyano, amino, heterocycle, and phenyl, (wherein the heterocycle or phenyl is unsubstituted or substituted by 1 or 2 substituents selected from the group consisting of halogen, hydroxy, cyano, carboxy and amino);

$R_1$ is hydrogen, hydroxy, —$OR_7$, —$CONHR_7$, or $C_1$–$C_6$ alkyl, in which the $C_1$–$C_6$ alkyl is unsubstituted or substituted by 1 or 2 substituents selected from the group consisting of carboxy, hydroxy, halogen, cyano, amino, heterocycle and phenyl, (wherein the phenyl is unsubstituted or substituted by 1 or 2 substituents selected from the group consisting of hydroxy, halogen, cyano, carboxy or amino);

wherein $R_7$ is selected from the group consisting of:
(i) $C_1$–$C_6$ alkyl which is unsubstituted or substituted by 1 or 2 substituents selected from the group consisting of hydroxy, halogen, cyano, amino, heterocycle, and phenyl, (wherein the phenyl is unsubstituted or substituted by 1 or 2 substituents selected from the group consisting of hydroxy, halogen, cyano, carboxy or amino), (ii) $C_2$–$C_4$ alkenyl which is unsubstituted or substituted by heterocycle or phenyl, (wherein the phenyl is unsubstituted or substituted by 1 or 2 substituents selected from the group consisting of hydroxy, halogen, cyano, amino and carboxy), (iii) $C_2$–$C_4$ alkynyl, (iv) $C_3$–$C_6$ cycloalkyl, (v) phenyl which is unsubstituted or substituted by 1, 2 or 3 substituents selected from the group consisting of hydroxy, halogen, carboxy, cyano, and amino, or (vi) a heterocycle which is monocyclic or bicyclic, preferably having 1, 2 or 3 heteroatoms selected from N, S, O, preferably selected from the group consisting of thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinoline, piperazine, N-methyl piperazine, morpholine, and thiomorpholine;

$R_2$ and $R_3$ are independently hydrogen or $C_1$–$C_3$ alkyl which is unsubstituted or substituted by 1 or 2 substituents independently selected from the group consisting of hydroxy and halogen;

n is 0, 1, or 2 and $n_1$ is 0 or 1.

In a preferred aspect of the present invention, $R_4$ is selected from the group consisting of hydrogen, —$COR_8$, —$COOR_9$, and —$SO_2R_{10}$, wherein:

$R_8$ is selected from the group consisting of: (i) $C_1$–$C_6$ alkyl which is unsubstituted or substituted by 1 or 2 substituents selected from the group consisting of hydroxy, halogen, cyano, amino, heterocycle (preferably selected from thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinoline, piperazine, N-methyl piperazine, morpholine, and thiomorpholine) and phenyl, (wherein the phenyl is unsubstituted or substituted by 1 or 2 substituents selected from the group consisting of hydroxy, halogen, cyano, carboxy and amino), (ii) $C_2$–$C_4$ alkenyl which is unsubstituted or substituted by heterocycle (preferably selected from thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinoline, piperazine, N-methyl piperazine, morpholine, and thiomorpholine) or phenyl, (wherein the phenyl is unsubstituted or substituted by 1 or 2 substituents selected from the group consisting of hydroxy, halogen, cyano, amino and carboxy), (iii) $C_2$–$C_4$ alkynyl, (iv) $C_3$–$C_6$ cycloalkyl, (v) phenyl which is unsubstituted or substituted by 1, 2 or 3 substituents selected from the group consisting of hydroxy, halogen, carboxy, cyano, and amino, or (vi) a heterocycle (preferably selected from thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinoline, piperazine, N-methyl piperazine, morpholine, and thiomorpholine);

$R_9$ is (i) $C_1$–$C_6$ alkyl which is unsubstituted or substituted with phenyl or heterocycle (preferably selected from thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinoline, piperazine, N-methyl piperazine, morpholine, and thiomorpholine) or (ii) phenyl;

$R_{10}$ is selected from the group consisting of (i) $C_1$–$C_6$ alkyl, (ii) alkenyl which is unsubstituted or substituted with heterocycle (preferably selected from thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinoline, piperazine, N-methyl piperazine, morpholine, thiomorpholine) or phenyl, (iii) phenyl which is unsubstituted or substituted by 1, 2 or 3 substituents selected from the group consisting of hydroxy, halogen, carboxy, cyano, amino, $C_1$–$C_4$ alkyl group, and $C_1$–$C_2$ alkoxy group, and (iv) naphthyl which is unsubstituted or substituted by 1, 2 or 3 substituents selected from hydroxy, halogen, cyano, carboxy, amino, $C_1$–$C_4$ alkyl group, and $C_1$–$C_2$ alkoxy group.

In another aspect, the present invention is directed to derivatives of general formula I, or pharmaceutically acceptable salts thereof, formula I

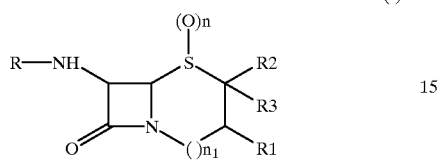

(I)

wherein
R is selected from the group consisting of
(a) a peptidyl residue of a single natural α-amino acid in either the L- or D-form, selected from the group consisting of D- or L-glycine, D- or L-alanine, D- or L-valine, D- or L-leucine, D- or L-isoleucine, D- or L-serine, D- or L-threonine, D- or L-aspartic acid, D- or L-glutamic acid, D- or L-asparagine, D- or L-glutamine, D- or L-lysine, D- or L-arginine, D- or L-phenylalanine, D- or L-tyrosine, D- or L-tryptophan, D- or L-histidine, D- or L-methionine, D- or L-proline, and
(b) a peptidyl residue of a single non-natural amino acid selected from the group consisting of D- or L-t-butyl alanine, D- or L-homophenyl alanine, D- or L-pyridyl alanine, D- or L-thienyl alanine, D- or L-naphthyl alanine, D- or L-methoxy phenylalanine, D- or L-halophenyl alanine, D- or L-ε-nitro arginine, D- or L-citrulline, D- or L-indoline carboxylic acid, D- or L-cycloalkyl glycine (e.g., cyclopentyl glycine), D- or L-cycloalkyl alanine (e.g., cyclohexyl alanine), D- or L-4-hydroxy-3-nitrophenylalanine, D- or L-4-amino-3,5-diiodophenyl alanine, D- or L-4-hydroxy-3,5-diiodophenyl alanine, D- or L-4-hydroxy-3,5-dibromo-phenyl alanine, D- or L-β-(3-benzothienyl) alanine, D- or L-3,4-dihydroxy-phenyl alanine, D- or L-3,4 (methylenedioxy)phenyl alanine, D- or L-3,4 (ethylenedioxy)phenyl alanine, D- or L-4,4'-biphenyl alanine, D- or L-3,4-dichlorophenyl alanine, D- or L-iodophenyl alanine, D- or L-4-nitrophenyl alanine, D- or L-pentafluorophenyl alanine, D- or L-trifluorophenyl alanine, D- or L-thiazolyl alanine, D- or L-trifluoromethylphenyl alanine, D- or L-sulfamoyl alanine, D- or L-t-butyloxy alanine, D- or L-1-t-butyloxymethylalanine, D- or L-trimethyl alanine, D- or L-3,4-diisopropyloxyphenyl alanine, D- or L-propylalanine, and D- or L-ethylalanine, in which peptidyl residue (a) or (b) the terminal —$NH_2$ group is unsubstituted or substituted once or twice with $R_4$,
wherein $R_4$ is selected from the group consisting of —$COOR_5$, —$COR_5$, —$SO_2R_5$, and —$COR_6$,
wherein $R_5$ is selected from the group consisting of (i) a $C_1$–$C_6$ alkyl group, (ii) a $C_2$–$C_6$ alkenyl group, (iii) a $C_2$–$C_6$ alkynyl group, (iv) a $C_3$–$C_6$ cycloalkyl group, (v) a phenyl group, (vi) a naphthyl group, and (vii) a monocyclic or bicyclic heterocyclic group, which group (i), (ii), (iii), (iv), (v), (vi), or (vii) is unsubstituted or substituted by 1, 2 or 3 substituents independently selected from the group consisting of
hydroxy,
halogen,
carboxy,
$C_1$–$C_4$ alkyl which is unsubstituted or substituted at least once with carboxy and/or amino,
$C_1$–$C_2$ alkoxy,
amino,
cyano,
phenyl which is unsubstituted or substituted by 1 or 2 substituents independently selected from the group consisting of hydroxy, halogen, carboxy, $C_1$–$C_4$ alkyl, $C_1$–$C_2$ alkoxy, amino, and cyano, and
a monocyclic or bicyclic heterocyclic group which is unsubstituted or substituted by 1 or 2 substituents independently selected from the group consisting of hydroxy, halogen, carboxy, $C_1$–$C_4$ alkyl, $C_1$–$C_2$ alkoxy, amino, and cyano;
and $R_6$ is an amino group which is unsubstituted or substituted at least once with a $C_1$–$C_6$ alkyl group which is unsubstituted or substituted by 1 or 2 substitutents selected from the group consisting of
hydroxy,
halogen,
cyano,
amino,
heterocycle which is unsubstituted or substituted by 1 or 2 substituents selected from the group consisting of halogen, hydroxy, cyano, carboxy and amino, and
phenyl which is unsubstituted or substituted by 1 or 2 substituents selected from the group consisting of halogen, hydroxy, cyano, carboxy and amino;
$R_1$ is selected from the group consisting of carboxy and $COOR_5$;
$R_2$ and $R_3$ are independently hydrogen or $C_1$–$C_3$ alkyl which is unsubstituted or substituted by 1 or 2 substituents independently selected from the group consisting of hydroxy and halogen;
n is 1 or 2; and
$n_1$ is 0 or 1.

In yet another aspect, the present invention is directed to derivatives of general formula I, or pharmaceutically acceptable salts thereof,

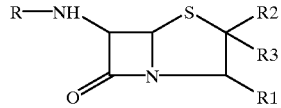

(I)

wherein
R is selected from the group consisting of
(a) a peptidyl residue of a single natural α-amino acid in either the L- or D-form, selected from the group consisting of D- or L-glycine, D- or L-alanine, D- or L-valine, D- or L-leucine, D- or L-isoleucine, D- or L-serine, D- or L-threonine, D- or L-aspartic acid, D- or L-glutamic acid, D- or L-asparagine, D- or L-glutamine, D- or L-lysine, D- or L-arginine, D- or L-phenylalanine, D- or L-tyrosine, D- or L-tryptophan, D- or L-histidine, D- or L-methionine, D- or L-proline, and
(b) a peptidyl residue of a single non-natural amino acid selected from the group consisting of D- or L-t-butyl alanine, D- or L-homophenyl alanine, D- or L-pyridyl alanine, D- or L-thienyl alanine, D- or L-naphthyl alanine, D- or L-methoxy phenylalanine, D- or L-halophenyl alanine, D- or L-ε-nitro arginine, D- or L-citrulline, D- or L-indoline carboxylic acid, D- or L-cycloalkyl glycine (e.g., cyclopentyl glycine), D- or L-cycloalkyl alanine (e.g., cyclohexyl alanine), D- or L-4-hydroxy-3-nitro-phenylalanine, D- or L4-amino-3,5-diiodophenyl alanine, D- or L4-hydroxy-3,5-diiodophenyl alanine, D- or L-4-hydroxy-3,5-dibromo-phenyl alanine, D- or L-β-(3-benzothienyl) alanine, D- or L-3,4-dihydroxy-phenyl alanine, D- or L-3,4 (methylenedioxy)phenyl alanine, D- or L-3,4 (ethylenedioxy)phenyl alanine, D- or L4,4'-biphenyl alanine, D- or L-3,4-dichlorophenyl alanine, D- or L-iodophenyl alanine, D- or L-4-nitrophenyl alanine, D- or L-pentafluorophenyl alanine, D- or L-trifluorophenyl alanine, D- or L-thiazolyl alanine, D- or L-trifluoromethylphenyl alanine, D- or L-sulfamoyl alanine, D- or L-t-butyloxy alanine, D- or L-1-t-butyloxymethylalanine, D- or L-trimethyl alanine, D- or L-3,4-diisopropyloxyphenyl alanine, D- or L-propylalanine, and D- or L-ethylalanine, in which peptidyl residue (a) or (b) the terminal —$NH_2$ group is unsubstituted or substituted once or twice with $R_4$, wherein $R_4$ is selected from the group consisting of —$COOR_5$, —$COR_5$, —$SO_2R_5$, and —$COR_6$, wherein $R_5$ is selected from the group consisting of (i) a $C_1$–$C_6$ alkyl group, (ii) a $C_2$–$C_6$ alkenyl group, (iii) a $C_2$–$C_6$ alkynyl group, (iv) a $C_3$–$C_6$ cycloalkyl group, (v) a phenyl group, (vi) a naphthyl group, and (vii) a monocyclic or bicyclic heterocyclic group, which group (i), (ii), (iii), (iv), (v), (vi), or (vii) is unsubstituted or substituted by 1, 2 or 3 substituents independently selected from the group consisting of
hydroxy,
halogen,
carboxy,
$C_1$–$C_4$ alkyl which is unsubstituted or substituted at least once with carboxy and/or amino,
$C_1$–$C_2$ alkoxy,
amino,
cyano,
phenyl which is unsubstituted or substituted by 1 or 2 substituents independently selected from the group consisting of hydroxy, halogen, carboxy, $C_1$–$C_4$ alkyl, $C_1$–$C_2$ alkoxy, amino, and cyano, and
a monocyclic or bicyclic heterocyclic group which is unsubstituted or substituted by 1 or 2 substituents independently selected from the group consisting of hydroxy, halogen, carboxy, $C_1$–$C_4$ alkyl, $C_1$–$C_2$ alkoxy, amino, and cyano;

and $R_6$ is an amino group which is unsubstituted or substituted at least once with a $C_1$–$C_6$ alkyl group which is unsubstituted or substituted by 1 or 2 substitutents selected from the group consisting of
hydroxy,
halogen,
cyano,
amino,
heterocycle which is unsubstituted or substituted by 1 or 2 substituents selected from the group consisting of halogen, hydroxy, cyano, carboxy and amino, and
phenyl which is unsubstituted or substituted by 1 or 2 substituents selected from the group consisting of halogen, hydroxy, cyano, carboxy and amino;

$R_1$ is selected from the group consisting of carboxy and $COOR_5$; and $R_2$ and $R_3$ are independently hydrogen or $C_1$–$C_3$ alkyl which is unsubstituted or substituted by 1 or 2 substituents independently selected from the group consisting of hydroxy and halogen.

The pharmaceutically acceptable salts of formula I include sodium, potassium, magnesium, calcium, hydrogen chloride, tartaric acid, succinic acid, fumaric acid and p-toluenesulfonic acid.

Amino bicyclic-β-lactam penam nucleus and substituted amino bicyclic-β-lactam cepham nucleus each carry two asymmetric carbon atoms at β-lactam, and can therefore exist as 4-diastereoisomers. In general, the preferred isomer is that in which the hydrogen atoms at β-lactam are trans to each other and this isomer has superior inhibitory activity against different cysteine proteases such as Cathepsin B, and Cathepsin L. Such diasterioisomers and their racemic mixtures are also included as cysteine protease inhibitors. In addition, there are other potentially asymmetric carbon atoms in the compounds according to the present invention, and the present invention in general covers all stereoisomers thereof.

Examples of preferred heterocyclic group or substituent as defined herein include $C_2$–$C_{11}$ monocyclic or bicyclic heterocyclic group which may have 1–3 heteroatoms selected from nitrogen, sulphur or oxygen.

As used herein "monocyclic heterocyclic" means a 5- or 6-membered aromatic or non-aromatic heterocyclic group containing 1, 2, 3 or 4 heteroatoms preferably selected from O, S or N; and "bicyclic heterocyclic" means a monocyclic heterocyclic as defined above which is fused to a second 5- or 6-membered carbocyclic or 5- or 6-membered heterocyclic ring. Preferred examples of such heterocyclic groups include, e.g., thiophene, pyridine, 1,2,3-triazole, 1,2,4-triazole, quinoline, benzofuran, benzothiophene, morpholine, thiomorpholine, piperazine, piperidine, thiazole, isothiazole, oxazole, isoxazole, imidazole, furan, pyrimidine, quinoline, isoquinoline, tetrahydroquinoline, tetrahydroisoquinoline, N-methyl piperazine, and the like.

More specifically, preferred embodiments of the present invention include the following compounds:

(5S,6R)-6-(2S-2-benzyloxycarbonylamino-2-phenylmethyl-acetamido)-4-thia-1-azabicyclo [3,2,0] heptan-7-one;

(5S,6R)-6-(2S-2-benzyloxycarbonylamino-2-phenylmethyl-acetamido)-4,4-dioxo-4-thia-1-azabicyclo [3,2,0] heptan-7-one;

(5R,6R)-6-(2S-2-benzyloxycarbonylamino-2-phenylmethyl-acetamido)-4,4-dioxo-4-thia-1-azabicyclo [3,2,0] heptan-7-one;

(5S,6R)-6-{2S-2-(3-phenylpropionoyl)amino-2-cyclohexylmethyl-acetamido}-4-thia-1-azabicyclo [3,2,0] heptan-7-one;

(5S,6R)-6-{2S-2-(3-phenylpropionoyl)amino-2-cyclohexylmethyl-acetamido}-4,4-dioxo-4-thia-1-azabicyclo [3,2,0] heptan-7-one;

(5S,6R)-6-{2S-2-(3-phenylpropionoyl)amino-2-(2-naphthyl)methyl-acetamido}- 4-thia-1-azabicyclo [3,2,0] heptan-7-one;

(5S,6R)-6-{2S-2-(3-phenylpropionoyl)amino-2-(2-naphthyl)methyl-acetamido}-4,4-dioxo-4-thia-1-azabicyclo [3,2,0] heptan-7-one;

(5S,6R)-6-{2S-2-(3-phenylpropionoyl)amino-2-(2-thienyl)methyl-acetamido}-4-thia-1-azabicyclo [3,2,0] heptan-7-one;

(5S,6R)-6-{2S-2-(3-phenylpropionoyl)amino-2-(2-thienyl)methyl-acetamido}-4,4-dioxo-4-thia-1-azabicyclo [3,2,0] heptan-7-one;

(5S,6R)-6-{2S-2-(3-phenylpropionoyl)amino-2-(3-fluorophenyl)methyl-acetamido}-4-thia-1-azabicyclo [3,2,0] heptan-7-one;

(5S,6R)-6-{2S-2-(3-phenylpropionoyl)amino-2-(3-fluorophenyl)methyl-acetamido}-4,4-dioxo-4-thia-1-azabicyclo [3,2,0] heptan-7-one;

(5S,6R)-6-(2S-2-benzyloxycarbonylamino-2-(3-pyridyl)methyl-acetamido}-4-thia-1-azabicyclo [3,2,0] heptan-7-one;

(5S,6R)-6-{2S-2-benzyloxycarbonylamino-2-(3-pyridyl)methyl-acetamido}-4,4-dioxo-4-thia-1-azabicyclo [3,2,0] heptan-7-one;

(6S,7R)-7-(2S-2-benzyloxycarbonylamino-2-phenylmethyl-acetamido)-5-thia-1-azabicyclo [4,2,0] octan-8-one;

(6S, 7R)-7-(2S-2-benzyloxycarbonylamino-2-phenylmethyl-acetamido)-5,5-dioxo-5-thia-1-azabicyclo [4,2,0] octan-8-one;

(6R,7R)-7-(2S-2-benzyloxycarbonylamino-2-phenylmethyl-acetamido)-5,5-dioxo-5-thia-1-azabicyclo [4,2,0] octan-8-one;

(6S,7R)-7-(2S-2-benzyloxycarbonylamino-2-phenylmethyl-acetamido)-3-hydroxy-5-thia-1-azabicyclo [4,2,0] octan-8-one;

Methyl (2S,5R,6R)-6-(2S-2-benzyloxycarbonylamino-2-phenylmethyl-acetamido)-3,3-dimethyl-7-oxo4,4-dioxo4-thia-1-azabicyclo[3,2,0]heptane-2-carboxylate;

(2S,5R,6R)-6-{2S-2-(3-phenylpropionoyl)amino-2-phenylmethyl-acetamido}-3,3-dimethyl-7-oxo-4,4-dioxo4-thia-1-azabicyclo [3,2,0] heptane-2-carboxylic acid;

(5S,6R)-6-{2R-2-benzyloxycarbonylamino-2-phenylmethyl-acetamido}-4,4-dioxo-4-thia-1-azabicyclo[3,2,0] heptan-7-one; and (5S,6R)-6-{2S-2-benzyloxycarbonylamino-2-phenylmethyl-acetamido}-4-oxo-4-thia-1-azabicyclo [3,2,0] heptan-7-one.

Compounds of formula I might be utilized for treatment of different diseases, including those referred to above.

DESCRIPTION OF PREFERRED EMBODIMENTS

The present invention relates to the substituted amino bicyclic-β-lactam penam derivatives and substituted amino bicyclic-β-lactam cepham derivatives having excellent cysteine protease inhibitory activity and selectivity among cysteine proteases. The compounds of this invention are characterized by having a substitution at position 6 of 4-thia-1-azabicyclo[3,2,0] heptan-7-one skeleton and at position 7 of 5-thia-1-azabicyclo[4,2,0] octan-8-one skeleton. The substituted amino bicyclic-β-lactam penam derivatives and substituted amino bicyclic-β-lactam cepham derivatives were prepared by the general synthetic route as represented in scheme I.

The derivatives of general formula I were prepared from the common intermediate 1. The preparation of compound I was carried out by a route comparable to that described in Eur. J. Med. Chem. 1992, 27, 131–140 starting from 6-aminopenicillanic acid.

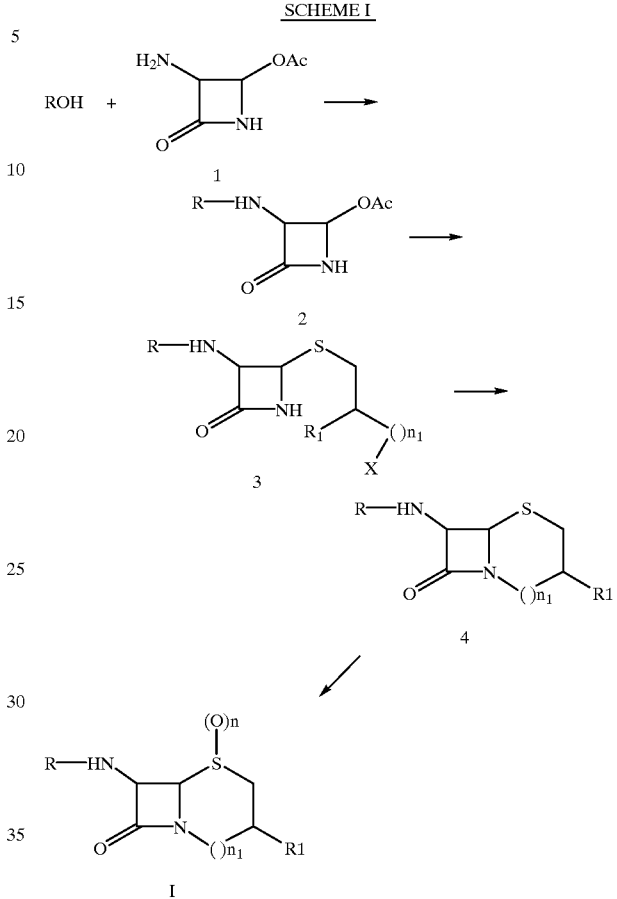

SCHEME I

The R group is an amino acid residue as defined above with a substitution at N-terminal. The intermediate 1 was coupled either with a unsubstituted or substituted amino acid residue in the presence of DCC, or with acid chloride in the presence of base, or with anhydride in the presence of base or activated ester. Compound 3 was obtained by reacting of 2 with mercapto alkanol in the presence of Lewis acids such as zinc acetate, zinc iodide, zinc chloride, titanium tetrachloride, palladium acetate, boron trifluoride, aluminum trichloride or in the presence of the base such as sodium hydroxide and potassium hydroxide and the like. X is a leaving group selected from a chlorine, bromine, iodine, methanesulfonyloxy or toluenesulfonyloxy group. Conversion of 3 to 4 was done by cyclization using a suitable base such as potassium carbonate, sodium carbonate, cesium carbonate in a non reactive solvent. Further compound 4 was oxidized to compound I using oxidizing agents such as m-chloroperbenzoic acid, potassium permanganate, hydrogen peroxide in organic acids such as formic or acetic acids. Depending upon the ratio of compound 4 and oxidizing agents, the compounds of formula I where n is 1 or 2 were obtained.

Alternatively, the derivatives of general formula I were also prepared by the general synthetic route as represented in scheme II.

The intermediate 5 was reacted with mercapto alkanol in the presence of Lewis acids such as zinc acetate, zinc iodide, zinc chloride, titanium tetrachloride, palladium acetate, boron trifluoride, aluminum trichloride or in the presence of base such as sodium hydroxide and the like. X is a leaving group selected from a chlorine, bromine, iodine, methanesulfonyloxy or toluenesulfonyloxy group to give compound 6. Cyclization of compound 6 using a suitable base such as potassium carbonate, sodium carbonate, cesium carbonate in a non reactive solvent gave protected compound 7. The benzyloxycarbonyl protected compound 7 was deprotected by hydrogenation in the presence of a metal catalyst, such as Pd, Pt, or Rh, under normal pressure to high pressure, gave compound 8. Further reaction of compound 8 with unsubstituted or substituted amino acid residue in the presence of DCC, or through acid chloride in the presence of base, or through anhydride in the presence of base or the activated ester, gave compound 9.

which were oxidized with oxidizing agents such as m-chloroperbenzoic acid, potassium permanganate, hydrogen peroxide in organic acids such as formic or acetic acids, gave the compound of general formula I. Depending upon the ratio of compound 9 and oxidizing agents, the compounds of formula I where n is 1 or 2 were obtained.

The compounds of general formula I where $R_1$ is $CONHR_7$ or $COOR_5$ were prepared by following the synthetic scheme as described in Scheme III. The starting compounds 10 were synthesized either by esterification of 6-amino penicillanic acid or by following a comparable procedure as described in literature. Compound 10 and N-substituted amino acid residues were coupled in the presence of DCC, or through acid chloride in the presence of base, or through anhydride in the presence of base or the activated ester, to give compound 11. The resulting coupled compound 11 was de-esterified and coupled with amines in presence of DCC or through acid chloride in the presence of base, or through anhydride in the presence of base or the activated ester.

-continued

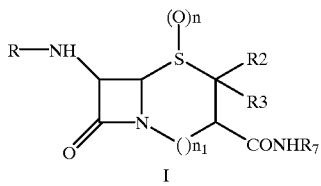

I

In the above processes, the reactants are reacted together with solvent at elevated or low temperatures for sufficient time to allow the reaction to proceed to completion. The reaction conditions will depend upon the nature and reactivity of the reactants. Wherever a base is used in a reaction, it is preferably selected from the group consisting of triethyl amine, pyridine, 4-dimethylaminopyridine, diisopropylamine, 1,5-diazabicyclo [4,3,0] non-5-ene, 1,8-diazabicyclo [5,4,0] undec-7-ene, sodium carbonate, potassium carbonate, cesium carbonate, sodium hydroxide, potassium hydroxide. Depending on the reactants, a solvent will generally be selected from the group consisting of benzene, toluene, acetonitrile, tetrahydrofuran, ethanol, methanol, chloroform, ethyl acetate, methylene chloride, dimethyl formamide, dimethyl sulfoxide, hexamethyl phosphoric triamide, water, pyridine, acetone and the like. Solvent mixtures may also be utilized. Reaction temperatures generally range from between −70° C. to 150° C. The preferred molar ratio of reactants are 1:1 to 5. The reaction time range from 0.5 to 72 hours, depending on the reactants.

The compounds of this invention, when used alone or in combination with other drugs as an agent for treating cancer (including cancer metastasis), osteoporosis, rheumatoid arthritis, muscular dystrophy, myocardial infarction, pulmonary emphysema, septic shock, cerebral ischemia, decreased memory function, Alzheimer, cataract, malaria, glomerular basement membrane degradation, bacterial infection, inflammatory diseases, parasitic infections and viral infections in mammals including humans, may take pharmaceutical dosage forms including parenteral preparation such as injections, suppositories, aerosols and the like, and oral preparations such as tablets, coated tablets, powders, granules, capsules, liquids and the like. Injections are generally preferred. The above preparations are formulated in a manner known in the art.

For the formulation of solid preparations for oral administration, an excipient, and if desired, a binder, disintegrator, lubricant, coloring agent, corrigent, flavor, etc. is added to the compound of the invention, and then tablets, coated tablets, granules, powders, capsules or the like are prepared in a conventional manner.

For the formulation of injections, a pH adjusting agent, buffer, stabilizer, isotonic agent, local anesthetic or the like is added to the active ingredient of the invention. Injections for subcutaneous, intramuscular or intravenous administration can be prepared in the conventional manner.

For the formulation of suppositories, a base, and, if desired, a surfactant are added to the active ingredient of the invention, and the suppositories are prepared in a conventional manner.

The excipients useful for solid preparations for oral administration are those generally used in the art, such as lactose, sucrose, sodium chloride, starches, calcium carbonate, kaolin, crystalline cellulose, methyl cellulose, glycerin, sodium alginate, gum arabic and the like. Other ingredients which may be used in the formulations of the invention include binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like; lubricants such as magnesium stearate, talc and the like; and additives such as usual known coloring agents, disintegrators and the like. Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspensions, solutions, syrups, elixirs and the like, which can be prepared by a conventional way using additives.

The amount of the compound of formula I of the invention to be incorporated into the pharmaceutical composition of the invention varies with the dosage form, solubility and chemical properties of the compound, administration route, administration scheme and the like. Preferably the amount is about 1 to 25 w/w % in the case of oral preparations, and about 0.1 to 5 w/w % in the case of injections which are parenteral preparations.

The dosage of the compound I of the invention is suitably determined depending on the individual cases taking symptoms, age and sex of the subject and the like into consideration. Usually the dosage in the case of oral administration is about 50 to 1500 mg per day for an adult in 2 to 4 divided doses, and the dosage in the case of injection, for example, by intravenous administration is 2.0 ml (about 1 to 100 mg) which is administratered once a day for adults wherein the injection may be diluted with physiological saline or glucose injection liquid if so desired, and slowly administered over at least 5 minutes. The dosage in case of suppositories is about 1 to 1000 mg which is administered once or twice a day at an interval of 6 to 12 hours wherein the suppositories are administered by insertion into the rectum.

EXAMPLE 1

(5S,6R)-6-(2S-2-benzyloxycarbonylamino-2-phenylmethyl-acetamido)-4-thia-1-azabicyclo [3,2, 0] heptan-7-one To a solution of mercaptoethanol (1.46 g, 18.7 mmol) in THF (40 ml), H$_2$O (40 ml) and 1N NaOH (18.7 ml), (3S,4S)-3-(2S-2-benzyloxycarbonylamino-2-phenylmethyl-acetamido)-4-acetoxy-azetidin-2-one (3.98 g, 9.365 mmol) in acetone (50 ml) and THF (50 ml) was slowly added at 5° C. The mixture was stirred at 5° C. for 2 hrs. After removal of solvent, the residue was dissolved in ethyl acetate, washed with water, brine and dried over sodium sulfate. After removal of solvent, the solid was washed with chloroform and ether and 3.79 g of crude (3R,4SR)-3-(2S-2-benzyloxycarbonylamino-2-phenylmethyl-acetamido)-4-hydroxyethylthio-azetidin-2-one was obtained.

To a solution of (3R,4SR)-3-(2S-2-benzyloxycarbonylamino-2-phenylmethyl-acetamido)-4-hydroxyethylthio-azetidin-2-one (3.79 g, 8.53 mmol) in pyridine (30 ml), p-toluenesulfonyl chloride (3.26 g, 17 mmol) was added at −15° C. The mixture was stirred at 5° C. for 6 hrs and then poured into 1N HCl (280 ml). The resulting solution was adjusted to pH 2 by addition of 1N HCl and extracted with ethyl acetate. The ethyl acetate was washed with cold saturated NaHCO$_3$ solution, water, brine and dried over sodium sulfate. After removal of solvent, the solid was washed with ether and 4.13 g of crude (3R,4SR)-3-(2S-2-benzyloxycarbonylamino-2-phenylmethyl-acetamido)-4-(4-methyl benzenesulfonyl)oxyethylthio-azetidin-2-one was obtained.

A mixture of (3R,4SR)-3-(2S-2-benzyloxycarbonylamino-2-phenylmethyl-acetamido)-4-(4-methylbenzenesulfonyl)oxyethylthio-azetidin-2-one (4.13 g, 6.92 mmol), lithium bromide (1.8 g, 21 mmol) and HMPA (25 ml) was stirred at 60° C. for 2 hrs. The resulting mixture was diluted with ethyl acetate, washed with water, brine, and dried over sodium sulfate. After removal of solvent, the residue was recrystallized from ethyl acetate and 1.40 g of (3R,4S)-3-(2S-2-benzyloxycarbonylamino-2-phenylmethyl-acetamido)-4-(2-bromoethyl)thio-azetidin-2-one was obtained.

Yield: 40%; $^1$H NMR (DMSO-d$_6$), δ (ppm): 2.70–2.85 (1H, m), 2.90–3.15 (3H, m), 3.60–3.75 (2H, m), 4.20–4.35 (1H, m), 4.55 (1H, d, J=8.1 Hz), 4.74 (1H, s), 4.94 (2H, m), 7.10–7.40 (10H, m), 7.58 (1H, d, J=8.6 Hz), 8.84 (1H, s), 8.88 (1H, d, J=8.1 Hz).

A mixture of (3R,4S)-3-(2S-2-benzyloxycarbonylamino-2-phenylmethyl-acetamido)-4-(2-bromoethyl)thio-azetidin-2-one (1.40 g, 2,767 mmol) and K$_2$CO$_3$ (420 mg, 3.0 mmol) and DMSO (20 ml) was stirred at room temperature overnight and then diluted with ethyl acetate, washed with water, brine, and dried over sodium sulfate. After removal of solvent, the residue was purified by silica gel column chromatography using methanol-chloroform (1:99) as eluent and the title compound was obtained.

Yield: 69%; $^1$H NMR (DMSO-d$_6$), δ (ppm): 2.70–3.20 (5H, m), 4.05–4.25 (2H, m), 4.66 (1H, d, J=8 Hz), 4.82 (1H, s), 4.96 (2H, m), 7.25–7.45 (10H, m), 7.62 (1H, d, J=8.4 Hz), 9.08 (1H, d, J=8 Hz).

EXAMPLE 2

(5S,6R)-6-(2S-2-benzyloxycarbonylamino-2-phenylmethyl-acetamido)-4,4-dioxo-4-thia-1-azabicyclo [3,2,0] heptan-7-one A mixture of (5S,6R)-6-(2S-2-benzyloxycarbonylamino-2-phenylmethyl-acetamido)-4-thia-1-azabicyclo [3,2,0] heptan-7-one (1.6 g, 3.76 mmol) and KMnO$_4$ (890 mg, 5.6 mmol) in acetic acid (60 ml) and water (15 ml) was stirred at 5° C. for 1 hr and then room temperature for 1 hr. H$_2$O$_2$ (30% aq) was added until brown color disappear. The reaction mixture was partitioned between ethyl acetate and water, the organic layer was washed with water, saturated NaHCO$_3$, water, brine and dried over Na$_2$SO$_4$. After removal of the solvent, solid was washed with ether and 1.12 g of the title compound was obtained.

Yield: 65%, m.p.: 122° C. (dec.); IR (KBr, cm$^{-1}$): 3290, 1781, 1683, 1652, 1522, 1310, 1250, 1230; $^1$H NMR (DMSO-d$_6$), δ (ppm): 2.70–2.85 (1H, m), 2.95–3.10 (1H, m), 3.45–3.70 (3H, m), 3.85–4.00 (1H, m), 4.15–4.30 (1H, m), 4.56 (1H, s), 4.95 (3H, m), 7.15–7.40 (10H, m), 7.68 (1H, d, J=8.4 Hz), 9.09 (1H, d, J=8 Hz); FAB-MS: 458 (MH$^+$), calcd for C$_{22}$H$_{23}$N$_3$O$_6$S 457.

EXAMPLE 3

(5R,6R)-6-(2S-2-benzyloxycarbonylamino-2-phenylmethyl-acetamido)-4,4-dioxo-4-thia-1-azabicyclo [3,2,0] heptan-7-one By a similar method as described in example 2, the title compound was obtained from (5R,6R)-6-(2S-2-benzyloxycarbonylamino-2-phenylmethyl-acetamido)-4-thia-1-azabicyclo [3,2,0] heptan-7-one.

Yield: 45%; m.p.: 181° C. (dec.); IR (KBr, cm$^{-1}$): 3365, 1781, 1693, 1511, 1307, 1224; $^1$H NMR (DMSO-d$_6$), δ (ppm): 2.70–2.85 (1H, m), 3.00–3.15 (1H, m), 3.50–3.75 (3H, m), 3.90–4.10 (1H, m), 4.30–4.45 (1H, m), 4.80 (1H, d, J=4.5 Hz), 4.94 (2H, s), 5.77 (1H, dd, J=4.5 and 8 Hz), 7.15–7.40 (10H, m), 7.71 (1H, d, J=8.5), 8.45 (1H, d, J=8 Hz); FAB-MS: 458 (MH$^+$), calcd for C$_{22}$H$_{23}$N$_3$O$_6$S 457.

EXAMPLE 4

(5S,6R)-6-{2S-2-(3-phenylpropionoyl)amino-2-cyclohexylmethyl-acetamido}-4-thia-1-azabicyclo [3,2,0] heptan-7-one By a similar method as described in example 1, the title compound was obtained from (3S,4S)-3-{2S-2-(3-phenylpropionoyl)amino-2-cyclohexyl methyl-acetam ido}-4-acetoxy-azetidin-2-one.

Yield: 85%; m.p.: 171–172° C.; IR (KBr, cm$^{-1}$): 3270, 2905, 1764, 1655, 1526, 1436, 1325; $^1$H NMR (DMSO-d$_6$), δ (ppm): 0.7–1.7 (13H, m), 2.35–2.50 (2H, m), 2.75–2.90 (3H, m), 3.05–3.25 (2H, m), 4.05–4.20 (1H, m), 4.25–4.40 (1H, m), 4.65 (1H, dd, J=1.8 and 8.0 Hz), 4.81 (1H, d, J=1.8 Hz), 7.15–7.30 (5H, m), 8.04 (1H, d, J=8.1 Hz), 8.92 (1H, d, J=8.0 Hz); FAB-MS: 430 (MH$^+$), calcd for C$_{23}$H$_{31}$N$_3$O$_3$S 429.

EXAMPLE 5

(5S,6R)-6-{2S-2-(3-phenylpropionoyl)amino-2-cyclohexylmethyl-acetamido}-4,4-dioxo-4-thia-1-azabicyclo [3,2,0] heptan-7-one By a similar method as described in example 2, the title compound was obtained from (5S,6R)-6-{2S-2-(3-phenylpropionoyl)amino-2-cyclohexylmethyl-acetamido}-4-thia-1-azabicyclo [3,2,0] heptan-7-one.

Yield: 79%; m.p.: 135° C. (dec.); IR (KBr, cm$^{-1}$): 3280, 2905, 1782, 1636, 1523, 1307, 1233; $^1$H NMR (DMSO-d$_6$), δ(ppm): 0.8–1.70 (13H, m), 2.35–2.45 (2H, m), 2.75–2.90 (2H, m), 3.40–3.65 (3H, m), 3.80–4.00 (1 H, m), 4.25–4.40 (1H, m), 4.54 (1H, d, J=1.7 Hz), 4.94 (1H, dd, J=1.7 and 8.0 Hz), 7.10–7.30 (5H, m), 8.08 (1 H, d, J=8.0 Hz), 8.93 (1 H, d, J=8.0 Hz); FAB-MS: 462 (MH$^+$), calcd for C$_{23}$H$_{31}$N$_3$O$_5$S 461.

EXAMPLE 6

(5S,6R)-6-{2S-2-(3-phenylpropionoyl)amino-2-(2-naphthyl)methyl-acetamido}-4-thia-1-azabicyclo [3,2,0] heptan-7-one By a similar method as described in example 1, the title compound was obtained from (3S,4S)-3-{2S-2-(3-phenylpropionoyl)amino-2-(2-naphthyl)methyl-acetamido}-4-acetoxy-azetidin-2-one.

Yield: 62%; m.p.: 161° C. (dec.); IR (KBr, cm$^{-1}$): 3380, 3265, 1768, 1635, 1527,1438,1372,1328,1222; $^1$H NMR (DMSO-d$_6$), δ (ppm): 2.30–2.40 (2H, m), 2.55–3.25 (7H, m), 4.05–4.20 (1H, m), 4.50–4.70 (1H, m), 4.62 (1H, d, J=8.2 Hz), 4.78 (1H, s), 7.00–7.20 (5H, m), 7.35–7.50 (3H, m), 7.70–7.90 (4H, m), 8.24 (1 H, d, J=8.3 Hz), 9.02 (1H, d, J=8.2 Hz); FAB-MS: 474 (MH$^+$), calcd for C$_{27}$H$_{27}$N$_3$O$_3$S 473.

EXAMPLE 7

(5S,6R)-6-{2S-2-(3-phenylpropionoyl)amino-2-(2-naphthyl)methyl-acetamido}-4,4-dioxo-4-thia-1-azabicyclo [3,2,0] heptan-7-one By a similar method as described in example 2, the title compound was obtained from (5S,6R)-6-{2S-2-(3- phenylpropionoyl)amino-2-(2-naphthyl)methyl-acetamido}-4-thia-1-azabicyclo [3,2,0] heptan-7-one.

Yield: 72%; m.p.: 138° C. (dec.); IR (KBr, cm$^{-1}$): 3370, 1778, 1642, 1513, 1309,1229; $^1$H NMR (DMSO-d$_6$), δ (ppm): 2.30–2.40 (2H, m), 2.55–2.70 (2H, m), 2.85–3.25 (2H, m), 3.45–3.65 (3H, m), 3.85–3.95 (1H, m), 4.56 (1H, s), 4.50–4.70 (1H, m), 4.94 (1H, d, J=8.0 Hz), 7.00–7.20 (5H, m), 7.35–7.50 (3H, m), 7.70–7.90 (4H, m), 8.29 (1H, d, J=8.1 Hz), 9.06 (1H, d, J=8.0 Hz); FAB-MS: 506 (MH$^+$), calcd for C$_{27}$H$_{27}$N$_3$O$_5$S 505.

EXAMPLE 8

(5S,6R)-6-{2S-2-(3-phenylpropionoyl)amino-2-(2-thienyl)methyl-acetamido}-4-thia-1-azabicyclo [3,2,0] heptan-7-one By a similar method as described in example 1, the title compound was obtained from (3S,4S)-3-{2S-2-(3-phenylpropionoyl)amino-2-(2-thienyl)methyl-acetamido}-4-acetoxy-azetidin-2-one.

Yield: 49%; m.p.: 188° C. (dec.); IR (KBr, cm$^{-1}$): 3290, 1778, 1651, 1525; $^1$H NMR (DMSO-d$_6$), δ (ppm): 2.35–2.45 (2H, m), 2.70–3.30 (7H, m), 4.05–4.20 (1H, m), 4.40–4.55 (1H, m), 4.62 (1H, d, J=7.9 Hz), 4.78 (1H, s), 6.80–6.95 (2H, m), 7.10–7.35 (6H, m), 8.23 (1H, d, J=8.2 Hz), 9.01 (1H, d, J=7.9 Hz); FAB-MS: 430 (MH$^+$), calcd for C$_{21}$H$_{23}$N$_3$O$_3$S$_2$ 429.

EXAMPLE 9

(5S,6R)-6-{2S-2-(3-phenylpropionoyl)amino-2-(2-thienyl)methyl-acetamido}-4,4-dioxo-4-thia-1-azabicyclo [3,2,0] heptan-7-one By a similar method as described in example 2, the title compound was obtained from (5S,6R)-6-{2S-2-(3-phenylpropionoyl)amino-2-(2-thienyl)methyl-acetamido}-4-thia-1-azabicyclo [3,2,0] heptan-7-one.

Yield: 38%; m.p.: 138° C. (dec.); IR (KBr, cm$^{-1}$): 3275, 1779, 1637, 1522, 1309,1228; $^1$H NMR (DMSO-d$_6$), δ (ppm): 2.35–2.45 (2H, m), 2.70–2.80 (2H, m), 2.95–3.30 (2H, m), 3.40–3.65 (3H, m), 3.85–4.00 (1H, m), 4.40–4.55 (1H, m), 4.52 (1H, s), 4.91 (1H, d, J=7.9 Hz), 6.80–6.95 (2H, m), 7.10–7.35 (6H, m), 8.27 (1H, d, J=8.2 Hz), 9.02 (1H, d, J=7.9 Hz); FAB-MS: 462 (MH$^+$), calcd for C$_{21}$H$_{23}$N$_3$O$_5$S$_2$ 461.

EXAMPLE 10

(5S,6R)-6-{2S-2-(3-phenylpropionoyl)amino-2-(3-fluorophenyl)methyl-acetamido}-4-thia-1-azabicyclo [3,2,0] heptan-7-one By a similar method as described in example 1, the title compound was obtained from (3S,4S)-3-{2S-2-(3-phenylpropionoyl)amino-2-(3-fluorophenyl)methyl-acetamido}-4-acetoxy-azetidin-2-one.

Yield: 84%; m.p.: 169–171° C.; IR (KBr, cm$^{-1}$): 3270, 1772, 1635, 1530; $^1$H NMR (DMSO-d$_6$), δ (ppm): 2.30–2.40 (2H, m), 2.60–3.20 (7H, m), 4.00–4.20 (1H, m), 4.40–4.55 (1H, m), 4.62 (1H, d, J=8 Hz), 4.77 (1H, s), 6.95–7.30 (9H, m), 8.20 (1H, d, J=8 Hz), 9.00 (1H, d, J=8 Hz); FAB-MS: 442 (MH$^+$), calcd for C$_{23}$H$_{24}$FN$_3$O$_3$S 441.

EXAMPLE 11

(5S,6R)-6-{2S-2-(3-phenylpropionoyl)amino-2-(3-fluorophenyl)methyl-acetamido}-4,4-dioxo-4-thia-1-azabicyclo [3,2,0] heptan-7-one By a similar method as described in example 2, the title compound was obtained from (5S,6R)-6-{2S-2-(3-phenylpropionoyl)amino-2-(3-fluorophenyl)methyl-acetamido}-4-thia-1-azabicyclo [3,2,0] heptan-7-one.

Yield: 81%; m.p.: 147° C. (dec.); IR (KBr, cm$^{-1}$): 3275, 1779, 1638, 1523, 1307,1249; $^1$H NMR (DMSO-d$_6$), δ (ppm): 2.30–2.40 (2H, m), 2.60–2.85 (3H, m), 3.00–3.10 (1H, m), 3.40–3.70 (3H, m), 3.85–4.05 (1H, m), 4.45–4.60 (2H, m), 4.94 (1H, d, J=7.8 Hz), 6.95–7.30 (9H, m), 8.28 (1H, d, J=8.3 Hz), 9.04 (1H, d, J=7.8 Hz); FAB-MS: 474 (MH$^+$), calcd for C$_{23}$H$_{24}$FN$_3$O$_5$S 473.

EXAMPLE 12

(5S,6R)-6-{2S-2-benzyloxycarbonylamino-2-(3-pyridyl)methyl-acetamido}-4-thia-1-azabicyclo [3,2,0] heptan-7-one By a similar method as described in example 1, the title compound was obtained from (3S,4S)-3-{2S-2-benzyloxycarbonylamino-2-(3-pyridyl)methyl-acetamido}-4-acetoxy-azetidin-2-one.

Yield: 51%, m.p.: 122° C. (dec.); IR (KBr, cm$^{-1}$): 3285, 1765, 1705, 1677, 1522, 1438, 1325, 1231; $^1$H NMR (DMSO-d$_6$), δ (ppm): 2.75–2.90 (2H, m), 2.95–3.25 (3H, m), 4.10–4.35 (2H, m), 4.67 (1H, d, J=7.8 Hz), 4.82 (1H, s), 4.94 (2H, m), 7.20–7.40 (6H, m), 7.65–7.75 (2H, m), 8.40–8.55 (2H, m), 9.10 (1H, d, J=7.8 Hz); FAB-MS: 427 (MH$^+$), calcd for C$_{21}$H$_{22}$N$_4$O$_4$S 426.

EXAMPLE 13

(5S,6R)-6-{2S-2-benzyloxycarbonylamino-2-(3-pyridyl)methyl-acetamido}-4,4-dioxo-4-thia-1-azabicyclo [3,2,0] heptan-7-one By a similar method as described in example 2, the title compound was obtained from (5S,6R)-6-{2S-2-benzyloxycarbonylamino-2-(3-pyridyl)methyl-acetamido}-4-thia-1-azabicyclo [3,2,0] heptan-7-one.

Yield: 69%; m.p.: 144° C. (dec.); IR (KBr, cm$^{-1}$): 3285, 1779, 1682, 1650, 1522, 1312, 1251, 1230; $^1$H NMR (DMSO-d$_6$), δ (ppm): 2.70–2.90 (1H, m), 3.00–3.20 (1H, m), 3.40–3.70 (3H, m), 3.85–4.10 (1H, m), 4.20–4.35 (1H, m), 4.57 (1H, s), 4.90–5.05 (3H, m), 7.15–7.40 (6H, m), 7.60–7.80 (2H, m), 8.40–8.55 (2H, m), 9.15 (1H, d, J=7.8 Hz); FAB-MS: 459 (MH$^+$), calcd for C$_{21}$H$_{22}$N$_4$O$_6$S 458.

EXAMPLE 14

(6S,7R)-7-(2S-2-benzyloxycarbonylamino-2-phenylmethyl-acetamido)-5-thia-1-azabicyclo [4,2,0] octan-8-one By a similar method as described in example 1, the title compound was obtained from (3S,4S)-3-(2S-2-benzyloxycarbonylamino-2-phenylmethyl-acetamido)-4-acetoxy-azetidin-2-one.

Yield: 36%; m.p.: 172–173° C.; IR (KBr, cm$^{-1}$): 3275, 1755, 1683,1650, 1526, 1439, 1384, 1251, 1229; $^1$H NMR (DMSO-d$_6$), δ (ppm): 1.80–2.00 (2H, m), 2.70–3.10 (5H, m), 3.75–3.90 (1H, m), 4.15–4.30 (1H, m), 4.55–4.65 (2H, m), 4.90–5.00 (2H, m), 7.15–7.35 (10H, m), 7.58 (1H, d, J=8.5 Hz), 9.03 (1H, d, J=8.0 Hz); FAB-MS: 440 (MH$^+$), calcd for C$_{23}$H$_{25}$N$_3$O$_4$S 439.

EXAMPLE 15

(6S,7R)-7-(2S-2-benzyloxycarbonylamino-2-phenylmethyl-acetamido)-5,5-dioxo-5-thia-1-azabicyclo [4,2,0] octan-8-one By a similar method as described in example 2, the title compound was obtained from (6S,7R)-7-{2S-2-(3- phenylpropionoyl)amino-2-phenylmethyl-acetamido}-5-thia-1-azabicyclo [4,2,0] octan-8-one.

Yield: 85%; m.p.: 156–157° C.; IR (KBr, cm$^{-1}$): 3295, 1769, 1679, 1520, 1440, 1381, 1308, 1278, 1235; $^1$H NMR (DMSO-d$_6$), δ (ppm): 2.05–2.20 (2H, m), 2.75–2.90 (1 H, m), 3.00–3.20 (2H, m), 3.40–3.80 (3H, m), 4.20–4.35 (1H, m), 4.95–5.05 (2H, m), 5.00 (1H, s), 5.12 (1H, d, J=8.2 Hz), 7.20–7.40 (10H, m), 7.69 (1H, d, J=8.4 Hz), 9.04 (1H, d, J=8.2 Hz); FAB-MS: 472 (MH$^+$), calcd for $C_{23}H_{25}N_3O_6S$ 471.

EXAMPLE 16

(6R,7R)-7-(2S-2-benzyloxycarbonylamino-2-phenylmethyl-acetamido)-5,5-dioxo-5-thia-1-azabicyclo [4,2,0] octan-8-one By a similar method as described in example 2, the title compound was obtained from (6R,7R)-7-{2S-2-(3-phenylpropionoyl)amino-2-phenylmethyl-acetamido)-5-thia-1-azabicyclo [4,2,0] octan-8-one.

Yield: 85%; m.p.: 191–192° C.; IR (KBr, cm$^{-1}$): 3355, 1754, 1699, 1509, 1441, 1383, 1308,1279, 1220; $^1$H NMR (DMSO-d$_6$), δ (ppm): 2.10–2.30 (2H, m), 2.70–2.90 (1H, m), 2.95–3.15 (2H, m), 3.25–3.40 (2H, m), 3.75–3.90 (1H, m), 4.30–4.45 (1H, m), 4.96 (2H, s), 5.06 (1H, d, J=4.4 Hz), 5.79 (1H, dd, J=4.4 and 9.9 Hz), 7.15–7.40 (10 H, m), 7.74 (1H, d, J=8.7 Hz), 8.47 (1H, d, J=9.9 Hz); FAB-MS: 472 (MH$^+$), calcd for $C_{23}H_{25}N_3O_6S$ 471.

EXAMPLE 17

(6S,7R)-7-(2S-2-benzyloxycarbonylamino-2-phenylmethyl-acetamido)-3-hydroxy-5-thia-1-azabicyclo [4,2,0] octan-8-one By a similar method as described in example 1, the title compound was obtained from (3S,4S)-3-(2S-2-benzyloxycarbonylamino-2-phenylmethyl-acetamido)-4-acetoxy-azetidin-2-one.

Yield: 27%; m.p.: 176–177° C.; IR (KBr, cm$^{-1}$): 3285, 1740, 1682, 1654, 1523, 1440,1390, 1251; $^1$H NMR (DMSO-d$_6$), δ (ppm): 2.65–2.85 (4H, m), 2.95–3.10 (1H, m), 3.55–3.70 (1H, m), 3.89 (1H, m), 4.20–4.35 (1H, m), 4.58 (1H, d, J=8.0 Hz), 4.60 (1H, s), 4.97 (2H, m), 5.56 (1H, d, J=4.5 Hz), 7.20–7.40 (10H, m), 7.59 (1H, d, J=8.5 Hz), 9.03 (1H, d, J=8.0 Hz); FAB-MS: 456 (MH$^+$), calcd for $C_{23}H_{25}N_3O_5S$ 455.

EXAMPLE 18

Methyl (2S,5R,6R)-6-(2S-2-benzyloxycarbonylamino-2-phenylmethyl-acetamido)-3,3-dimethyl-7-oxo-4,4-dioxo4-thia-1-azabicyclo[3,2,0]heptane-2-carboxylate Methyl (2S,5R,6R)-6-benzyloxycarbonylamino-3,3-dimethyl-7-oxo-4-thia-1-azabicyclo [3,2,0] heptane-2-carboxylate (364 mg, 1 mmol) was hydrogenated with about 1.5 g of 10% palladium on activated carbon in 25 ml of ethyl acetate at 50 psi hydrogen pressure at room temperature for 10 hrs. After removal of catalyst by filtration, deprotected methyl (2S,5R,6R)-6-amino-3,3-dimethyl-7-oxo-4-thia-1-azabicyclo [3,2,0] heptane-2-carboxylate in ethyl acetate was obtained.

To a solution of 2S-2-benzyloxycarbonylamino-2-phenylmethyl-acetic acid (299 mg, 1 mmol) and 1-hydroxybenzotriazole (135 mg, 1 mmol) in THF (10 ml), DCC (206 mg, 1 mmol)/THF (5 ml) was added at 0° C. The reaction mixture was stirred at room temperature for 1.5 hrs and then cooled with an ice bath. The resulting DCU was removed by filtration. Then a precooled solution methyl (2S,5R,6R)-6-amino-3,3-dimethyl-7-oxo-4-thia-1-azabicyclo [3,2,0] heptane-2-carboxylate in ethyl acetate was added at −15° C. and the resulting mixture was stirred at a bath temperature of −15 to 5° C. for 1 hr and then at room temperature for 3 hrs. After removal of solvent, the residue was dissolved in ethyl acetate, washed with cold saturated NaHCO$_3$ solution, water, brine and dried over sodium sulfate. after removal of solvent, the residue was purified by silica gel column chromatography using hexane-ethyl acetate (1:3) as eluent and methyl (2S,5R,6R)-6-(2S-2-benzyloxycarbonylamino-2-phenylmethyl-acetamido)-3,3-dimethyl-7-oxo-4-thia-1-azabicyclo [3,2,0] heptane-2-carboxylate was obtained.

Yield: 13%; $^1$H NMR (CDCl$_3$), δ (ppm): 1.44 (3H, s), 1.50 (3H, s), 3.08 (2H, d, J=6.9 Hz), 3.77 (3H, s), 4.39 (1H, s), 4.45–4.55 (1H, m), 5.09 (2H, s), 5.32 (1H, br), 5.49 (1H, d, J=4.2 Hz), 5.62 (1H, dd, J=8.8 and 4.2 Hz), 6.60 (1H, d, J=8.8 Hz), 7.20–7.40 (10H, m).

A mixture of methyl (2S,5R,6R)-6-(2S-2-benzyloxycarbonylamino-2-phenylmethyl-acetamido)-3,3-dimethyl-7-oxo-4-thia-1-azabicyclo [3,2,0] heptane-2-carboxylate (64 mg, 0.12 mmol) and KMnO$_4$ (37 mg, 0.24 mmol) in acetic acid (2 ml) and water (0.5 ml) was stirred at 5° C. for 1 hr and then room temperature for 1 hr. One drop of H$_2$O$_2$ (30% aq) was added. The reaction mixture was partitioned between ethyl acetate and water, the organic layer was washed with water, saturated NaHCO$_3$, water, brine and dried over Na$_2$SO$_4$. After removal of the solvent, solid was washed with ether and 52 mg of the title compound was obtained.

Yield: 77%; m.p.: 85° C. (dec.); IR (KBr, cm$^{-1}$): 3375, 1790, 1745, 1687, 1504,1313,1214; $^1$H NMR (CDCl$_3$), δ (ppm): 1.38 (3H, s), 1.58 (3H, s), 3.00–3.25 (2H, m), 3.83 (3H, s), 4.47 (1H, s), 4.45–4.55 (1H, m), 4.75 (1H, d, J=4.6 Hz), 5.09 (2H, s), 5.17 (1H, d, J=10 Hz), 6.05 (1H, dd, J=10 and 4.6 Hz), 7.10–7.40 (11H, m); FAB-MS: 544 (MH$^+$), calcd for $C_{26}H_{29}N_3O_8S$ 543.

EXAMPLE 19

(2S,5R,6R)-6-{2S-2-(3-phenylpropionoyl)amino-2-phenylmethyl-acetamido}-3,3-dimethyl-7-oxo-4,4-dioxo-4-thia-1-azabicyclo [3,2,0] heptane-2-carboxylic acid To a solution of 2S-2-(3-phenylpropionoyl)amino-2-phenylmethyl-acetic acid (594 mg, 2 mmol) and 1-hydroxybenzotriazole (270 mg, 2 mmol) in THF (10 ml), DCC (412 mg, 2 mmol)/THF (5 ml) was added at 0° C. The reaction mixture was stirred at room temperature for 1.5 hrs and then cooled with an ice bath. The resulting DCU was removed by filtration. Then a precooled solution diphenylmethyl (2S,5R,6R)-6-amino-3,3-dimethyl-7-oxo-4-thia-1-azabicyclo [3,2,0] heptane-2-carboxylate (764 mg, 2mmol) in THF (10 ml) was added at −15° C. and the resulting mixture was stirred at a bath temperature of −15 to 5° C. for 1 hr and then at room temperature overnight. After removal of solvent, the residue was dissolved in ethyl acetate, washed with cold saturated NaHCO$_3$ solution, water, brine and dried over sodium sulfate, after removal of solvent, the residue was purified by silica gel column chromatography using hexane-ethyl acetate (2:1) as eluent and diphenyl methyl (2S,5R,6R)-6-{2S-2-(3-phenylpropionoyl)amino-2- phenylmethyl-acetamido}-3,3-dimethyl-7-oxo-4-thia-1-azabicyclo [3,2,0] heptane-2-carboxylate was obtained.

Yield: 80%; $^1$H NMR (CDCl$_3$), δ (ppm): 1.22 (3H, s), 1.47 (3H, s), 2.40–2.55 (2H, m), 2.85–3.05 (4H, m), 4.49 (1H, s), 4.60–4.70 (1H, m), 5.45–5.65 (2H, m), 5.96 (1H, d, J=7.6 Hz), 6.47 (1H, d, J=9.0 Hz), 6.92 (1H, s), 7.10–7.40 (20H, m).

A mixture of diphenylmethyl (2S,5R,6R)-6-{2S-2-(3-phenylpropionoyl)amino-2-phenylmethyl-acetamido}-3,3-dimethyl-7-oxo-4-thia-1-azabicyclo [3,2,0] heptane-2-carboxylate (600 mg, 0.86 mmol) and KMnO$_4$ (226 mg, 1.43 mmol) in acetic acid (8 ml) and water (2 ml) was stirred at 5° C. for 1 hr and then room temperature for 1 hr. One drop of H$_2$O$_2$ (30% aq) was added. The reaction mixture was partitioned between ethyl acetate and water, the organic layer was washed with water, saturated NaHCO$_3$, water, brine and dried over Na$_2$SO$_4$. After removal of solvent, the residue was purified by silica gel column chromatography using hexane-ethyl acetate (2:1) as eluent and diphenylmethyl (2S,5R,6R)-6-{2S-2-(3-phenylpropionoyl)amino-2-phenylmethyl-acetamido}-3,3-dimethyl-7-oxo-4,4-dioxo-4-thia-1-azabicyclo [3,2,0] heptane-2-carboxylate was obtained.

Yield: 53%; $^1$H NMR (CDCl$_3$), δ (ppm): 1.06 (3H, s), 1.55 (3H, s), 2.40–2.55 (2H, m), 2.85–3.05 (4H, m), 4.56 (1H, s), 4.69 (1H, d, J=4.5 Hz), 4.70–4.80 (1H, m), 5.84 (1H, d, J=7.7 Hz), 6.02 (1H, dd, J=4.5 and 10.2 Hz), 6.98 (1H, s), 7.05–7.45 (21 H, m).

Diphenylmethyl (2S,5R,6R)-6-{2S-2-(3-phenylpropionoyl)amino-2-phenylmethyl-acetamido}-3,3-dimethyl-7-oxo-4,4-dioxo-4-thia-1-azabicyclo (3,2,0] heptane-2-carboxylate (100 mg, 0.15 mmol) was added to a mixture of dichloromethane (1 ml)/TFA (2 ml)/anisole (1 ml) at −15° C. The resulting mixture was stirred at −15 to −5° C. for 1.5 hrs. After removal of solvent under vacuum, the residue was dissolved in ether and precipitated by adding hexane. The title compound was obtained as solid.

Yield: 57%; m.p.: 124° C. (dec.); IR (KBr, cm$^{-1}$): 3370, 1798, 1733, 1644, 1508,1312, 1214; $^1$H NMR (DMSO-d$_6$), δ (ppm): 1.38 (3H, s), 1.49 (3H, s), 2.25–2.35 (2H, m), 2.65–2.85 (4H, m), 4.41 (1H, s), 4.60–4.75 (1H, m), 5.41 (1H, d, J=4.5 Hz), 5.93 (1H, dd, J=4.5 and 9.1 Hz), 7.05–7.40 (10H, m), 8.29 (1H, d, J=8.5 Hz), 8.42 (1H, d, J=9.1 Hz); FAB-MS: 528 (MH$^+$), calcd for C$_{26}$H$_{29}$N$_3$O$_7$S 527.

EXAMPLE 20

(5S,6R)-6{2R-2-benzyloxycarbonylamino-2-phenylmethyl-acetamido}-4,4-dioxo4-thia-1-azabicyclo[3,2,0] heptan-7-one By a similiar method as described in example 2, the title compound was obtained from (5S,6R)-6-{2R-2-benzyloxycarbonylamino-2-phenylmethyl-acetamido}4-thia-1-azabicyclo [3,2,0] heptan-7-one.

Yield: 70% m.p.: 114–115° C. $^1$H NMR (DMSO-d$_6$), δ (ppm): 2.70–2.90 (1H m), 2.95–3.10 (1H, m), 3.40–3.70 (3H, m), 3.85–4.05 (1H, m), 4.15–4.30 (1H, m), 4.43 (1H, d, J=1.6 Hz), 4.96 (2H, m), 5.02 (1H, dd, J=1.6 and 6.5 Hz), 7.20–7.40 (10H, m), 7.69 (1H, d, J=8.2 Hz), 9.12 (IH, d, J=8.2 Hz). FAB-MS: 456 (MH+), calcd for C$_{22}$H$_{23}$N$_3$O$_6$S 457.

EXAMPLE 21

(5S,6R)-6-{2S-2-benzyloxycarbonylamino-2-phenylmethyl-acetamido}-4-oxo-4-thia-1-azabicyclo [3,2,0] heptan-7-one A mixture of hydrogen peroxide (30% w/w, 17 mg, 0.15 mmole), acetic acid (24 mg, 0.4 mmole) was added to a stirred solution of (5S,6R)-6-{2S-2-benzyloxycarbonyl amino-2-phenylmethyl-acetamido}-4-thia-1-azabicyclo [3,2,0] heptan-7-one (example 1) (43 mg, 0.1 mmole) in dichloromethane (3 ml). The reaction mixture was stirred at room temperature for 48 hr and then purified by silica gel column chromatography using methanol-chloroform (2.5:100) as eluent and 20 mg of the title compound was obtained.

Yield: 45% m.p.: 190° C. (dec.) $^1$H NMR (DMSO-d$_6$), δ (ppm): 2.70–3.10 (2H m), 3.15–3.65 (3H,m), 3.70–3.90 (1H, m), 4.15–4.35 (1H, m), 4.85 (1H, d, J=8.1 Hz), 4.92 (1H, s), 4.95 (2H, m), 7.15–7.40 (10H, m), 7.65 (1H, d, J=8.5 Hz), 9.06 (1H, d, J=8.2 Hz). FAB-MS: 442 (MH$^+$), calcd for C$_{22}$H$_{23}$N$_3$O$_5$S 441.

Testing of Inhibitors for Inhibition of Cathepsin B and L

TEST EXAMPLE 1

In Vitro Assay Procedure for Cathepsin B

The compounds of formula I were tested for inhibition of cathepsin B using the known method (A. J. Barret et al., Biochem. J. 1982, 201, 189–198). To a 170 μl of enzyme-buffer mixture (enzyme: r rat cathepsin B, diluted to give approximate 10 F units/min, buffer: 56 mM sodium acetate, 1.124 mM EDTA, 10 mM DTT, pH 5.1) a 10 μl of inhibitor (dissolved in DMSO) was added. After 10 min of incubation at room temperature, a 20 μl of 5 mM substrate (N-CBZ-Phe-Arg-AMC, dissolved in DMSO) was added to initiate reaction. Reading is followed up for 10 min at the fluoroscan reader (excitation at 380 nm emission at 460 nm).

A plot of percentage of inhibition vs inhibitor concentration is obtained, and IC$_{50}$ is determined using a linear regression calculation (concentration of inhibitor which will give 50% inhibition).

TEST EXAMPLE 2

In Vitro Assay Procedure for Cathepsin L

To a 170 μl of enzyme-buffer mixture (enzyme: r rat cathepsin L, diluted to give approximate 15 F units/min, buffer: 58.8 mM sodium citrate, 1.18 mM EDTA, 235 mM sodium chloride, 5 mM DTT, pH 5.0) a 10 μL of inhibitor (dissolved in DMSO) was added. After 10 min of incubation at room temperature, a 20 μl of 1 mM substrate (N-CBZ-Phe-Arg-AMC, dissolved in DMSO) was added to initiate reaction. Reading is followed up for 10 min at the fluoroscan reader (excitation at 380 nm emission at 460 nm).

A plot of percentage of inhibition vs inhibitor concentration is obtained, and IC$_{50}$ is determined using a linear regression calculation (concentration of inhibitor which will give 50% inhibition).

TABLE 1

In vitro inhibitory activity of example compounds on cysteine proteases

| | IC$_{50}$ (μM) | |
|---|---|---|
| Example No. | Cathepsin B | Cathepsin L |
| 1 | >50 | 6.68 |
| 2 | 0.35 | 0.0014 |
| 3 | 6.01 | 0.0096 |
| 4 | >50 | >50 |

TABLE 1-continued

In vitro inhibitory activity of example compounds on cysteine proteases

| Example No. | IC$_{50}$ ($\mu$M) | |
| --- | --- | --- |
| | Cathepsin B | Cathepsin L |
| 5 | 0.43 | 0.0007 |
| 6 | 10.5 | 0.43 |
| 7 | 0.39 | 0.003 |
| 8 | >50 | 11.63 |
| 9 | 0.43 | 0.003 |
| 10 | >50 | 11.32 |
| 11 | 1.0 | 0.0033 |
| 12 | >50 | 11.7 |
| 13 | 1.3 | 0.0017 |
| 14 | >50 | >50 |
| 15 | >50 | 2.12 |
| 16 | >50 | >50 |
| 17 | >50 | 2.19 |
| 18 | 28.2 | 1.74 |
| 19 | >50 | 6.77 |
| 20 | >50 | 0.044 |
| 21 | 16.37 | 0.068 |

What is claimed is:

1. A compound of formula I, or a pharmaceutically acceptable salt thereof,

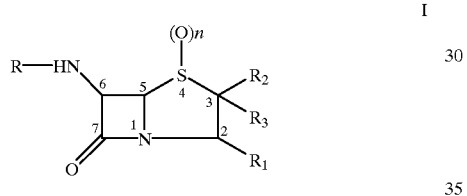

I wherein $R_1$ is hydrogen or $C_1$–$C_6$ alkyl which is unsubstituted or substituted by 1 or 2 substituents selected from the group consisting of
carboxy,
hydroxy,
halogen,
cyano,
amino,
a monocyclic or bicyclic heterocyclic group, wherein the monocyclic heterocyclic group is a 5- or 6-membered aromatic or non-aromatic ring containing 1–4 heteroatoms each selected from the group consisting of O, S and N, with the remainder of the atoms in the ring being carbon, and the bicyclic heterocyclic group is an 8- to 10-membered ring consisting of a monocyclic heterocyclic group, as defined above, which is fused to a second monocyclic heterocyclic group, as defined above, or a 5- or 6-membered carbocyclic group and
phenyl, wherein the phenyl is unsubstituted or substituted by 1 or 2 substituents selected from the group consisting of hydroxy, halogen, cyano, carboxy and amino;

$R_2$ and $R_3$ are independently hydrogen or $C_1$–$C_3$ alkyl which is unsubstituted or substituted by 1 or 2 substituents independently selected from the group consisting of hydroxy and halogen;

n is 0, 1, or 2; and

R is selected from the group consisting of
(a) a peptidyl residue of a single natural α-amino acid in either the L- or D-form, selected from the group consisting of glycine, alanine, valine, leucine, isoleucine, serine, threonine, aspartic acid, glutamic acid, asparagine, glutamine, lysine, arginine, phenylalanine, tyrosine, tryptophan, histidine, methionine and proline, and
(b) a peptidyl residue of a single non-natural amino acid in either the L- or D-form, selected from the group consisting of t-butylalanine, homophenylalanine, pyridylalanine, thienylalanine, naphthylalanine, methoxyphenylalanine, halophenylalanine, Nω-nitroarginine, citrulline, indoline carboxylic acid, cycloalkylglycine, cycloalkylalanine, 4-hydroxy-3-nitrophenylalanine, 4-amino-3,5-diiodophenylalanine, 4-hydroxy-3,5-diiodophenylalanine, 4-hydroxy-3,5-dibromophenylalanine, β-(3-benzothienyl)alanine, 3,4-dihydroxyphenylalanine, 3,4(methylenedioxy)phenylalanine, 3,4(ethylenedioxy)phenylalanine, 4,4'-biphenylalanine, 3,4-dichlorophenylalanine, iodophenylalanine, 4-nitrophenylalanine, pentafluorophenylalanine, trifluorophenylalanine, thiazolylalanine, trifluoromethylphenylalanine, sulfamoylalanine, t-butyloxyalanine, β-t-butyloxy-β-methylalanine, 3,4-diisopropyloxyphenylalanine, propylalanine and ethylalanine, wherein the terminal —NH$_2$ group in peptidyl residue (a) or (b) is unsubstituted or substituted once or twice with $R_4$, wherein $R_4$ is selected from the group consisting of —COOR$_5$, —COR$_5$, —SO$_2$R$_5$, and —COR$_6$, wherein $R_5$ is selected from the group consisting of
(i) a $C_1$–$C_6$ alkyl group,
(ii) a $C_2$–$C_6$ alkenyl group,
(iii) a $C_2$–$C_6$ alkynyl group,
(iv) a $C_3$–$C_6$ cycloalkyl group,
(v) a phenyl group,
(vi) a naphthyl group and
(vii) a monocyclic or bicyclic heterocyclic group, wherein the monocyclic heterocyclic group is a 5- or 6-membered aromatic or non-aromatic ring containing 1–4 heteroatoms each selected from the group consisting of O, S and N, with the remainder of the atoms in the ring being carbon, and the bicyclic heterocyclic group is an 8- to 10-membered ring consisting of a monocyclic heterocyclic group, as defined above, which is fused to a second monocyclic heterocyclic group, as defined above, or a 5- or 6-membered carbocyclic group, wherein group (i), (ii), (iii), (iv), (v), (vi) or (vii) is unsubstituted or substituted by 1, 2 or 3 substituents independently selected from the group consisting of
hydroxy,
halogen,
carboxy,
$C_1$–$C_4$ alkyl which is unsubstituted or substituted at least once with carboxy and/or amino,
$C_1$–$C_2$ alkyoxy,
amino,
cyano,
phenyl which is unsubstituted or substituted by 1 or 2 substituents independently selected from the group consisting of hydroxy, halogen, carboxy, $C_1$–$C_4$ alkyl, $C_1$–$C_2$ alkoxy, amino and cyano and
a monocyclic or bicyclic heterocyclic group, wherein the monocyclic heterocyclic group is a 5- or 6-membered aromatic or non-aromatic ring containing 1–4 heteroatoms each selected from the group consisting of O, S and N, with the remainder of the atoms in the ring being carbon, and the bicyclic heterocyclic group is an 8- to 10-membered ring consisting of a monocyclic heterocyclic group, as defined above, which is fused to a second monocyclic heterocyclic group, as defined above, or a 5- or 6-membered carbocyclic group, which monocyclic or bicyclic heterocyclic group is unsubstituted or substituted by 1 or 2 substituents independently selected from the group consisting of hydroxy, halogen, carboxy, $C_1-C_4$ alkyl, $C_1-C_2$ alkoxy, amino and cyano and $R_6$ is an amino group which is unsubstituted or substituted at least once with a $C_1-C_6$ alkyl group which is unsubstituted or substituted by 1 or 2 substituents selected from the group consisting of hydroxy, halogen, cyano, amino, a monocyclic or bicyclic heterocyclic group, wherein the monocyclic heterocyclic group is a 5- or 6-membered aromatic or non-aromatic ring containing 1–4 heteroatoms each selected from the group consisting of O, S and N, with the remainder of the atoms in the ring being carbon, and the bicyclic heterocyclic group is an 8- to 10-membered ring consisting of a monocyclic heterocyclic group, as defined above, which is fused to a second monocyclic heterocyclic group, as defined above, or a 5- or 6-membered carbocyclic group, wherein the monocyclic or bicyclic heterocyclic group is unsubstituted or substituted by 1 or 2 substituents selected from the group consisting of halogen, hydroxy, cyano, carboxy and amino and phenyl which is unsubstituted or substituted by 1 or 2 substituents selected from the group consisting of halogen, hydroxy, cyano, carboxy and amino.

2. A compound or salt as recited in claim 1, wherein $R_4$ is selected from the group consisting of hydrogen, —$COR_8$, —$COOR_9$, and —$SO_2R_{10}$, wherein $R_8$ is selected from the group consisting of: (i) $C_1-C_6$ alkyl which is unsubstituted or substituted by 1 or 2 substituents selected from the group consisting of hydroxy, halogen, cyano, amino, heterocycle, and phenyl, wherein the heterocycle is selected from the group consisting of thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinolirie, piperazine, N-methyl piperazine, morpholine, and thiomorpholine, and wherein the phenyl is unsubstituted or substituted by 1 or 2 substituents selected from the group consisting of hydroxy, halogen, cyano, carboxy and amino, (ii) $C_2-C_4$ alkenyl which is unsubstituted or substituted by heterocycle or phenyl, wherein the heterocycle is selected from the group consisting of thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinoline, piperazine, N-methyl piperazine, morpholine, and thiomorpholine, and wherein the phenyl is unsubstituted or substituted by 1 or 2 substituents selected from the group consisting of hydroxy, halogen, cyano, amino and carboxy, (iii) $C_2-C_4$ alkynyl, (iv) $C_3-C_6$ cycloalkyl, (v) phenyl which is unsubstituted or substituted by 1, 2 or 3 substituents selected from the group consisting of hydroxy, halogen, carboxy, cyano, and amino, and (vi) a heterocycle selected from the group consisting of thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinoline, piperazine, N-methyl piperazine, morpholine, and thiomorpholine;

$R_9$ is (i) $C_1-C_6$ alkyl which is unsubstituted or substituted with phenyl or heterocycle, wherein the heterocycle is selected from the group consisting of thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinoline, piperazine, N-methyl piperazine, morpholine, and thiomorpholine, or (ii) phenyl;

$R_{10}$ is selected from the group consisting of (i) $C_1-C_6$ alkyl, (ii) alkenyl which is unsubstituted or substituted with heterocycle or phenyl, wherein the heterocycle is selected from the group consisting of thiazole, isothiazole, oxazole, isoxazole, 1,2,4-triazole, 1,2,3-triazole, imidazole, furan, pyridine, pyrimidine, quinoline, isoquinoline, tetrahydroquinoline, tetrahydroisoquinoline, piperazine, N-methyl piperazine, morpholine, and thiomorpholine, (iii) phenyl which is unsubstituted or substituted by 1, 2 or 3 substituents selected from the group consisting of hydroxy, halogen, carboxy, cyano, amino, $C_1-C_4$ alkyl group, and $C_1-C_2$ alkoxy group, and (iv) naphthyl which is unsubstituted or substituted by 1, 2 or 3 substituents selected from the group consisting of hydroxy, halogen, cyano, carboxy, amino, $C_1$–C4 alkyl group, and $C_1-C_2$ alkoxy group.

3. A compound or salt as recited in claim 1, wherein the hydrogen atoms bonded to the carbon atoms at the 5- and 6-positions are trans to each other.

4. A method of regulating a cysteine protease selected from the group consisting of Cathepsin B and Cathepsin L in a patient in need of arthritis treatment, comprising administering to said patient a compound or salt as recited in claim 1 in an amount which is effective at treating arthritis.

5. A compound or salt as recited in claim 1, wherein each of said $C_1-C_6$ alkyl groups independently is a straight or branched chain alkyl group having 1 to 6 carbon atoms and being selected from the group consisting of methyl, ethyl, propyl, pentyl, hexyl, 2-methyl propyl, 3-methyl butyl, 4-methyl pentyl, 1-methyl propyl, 1-methyl butyl, 2-methyl butyl, and 1-methyl pentyl.

6. A compound or salt as recited in claim 1, wherein each of said $C_1-C_4$ alkyl groups independently is a straight or branched chain alkyl group having 1 to 4 carbon atoms and being selected from the group consisting of methyl, ethyl, propyl, butyl, 2-methyl propyl, and 1- thyl propyl.

7. A compound or salt as recited in claim 1, wherein each said $C_2-C_4$ alkenyl group independently is a straight chain alkenyl group having 2–4 carbon atoms and being selected from the group consisting of ethenyl, 1-propenyl, 1-butenyl, 2-butenyl, and 1,3 butadienyl.

8. A compound or salt as recited in claim 1, wherein $R_1$, $R_2$ and $R_3$ are each hydrogen.

9. A compound or salt as recited in claim 1, wherein said peptidyl residue of a single natural α-amino acid or said peptidyl residue of a single non-natural amino acid is in the L stereoisomeric form.

10. A compound or salt as recited in claim 1, herein $R_4$ is selected from the group consisting of benzyloxycarbonyl and 3-phenylpropionoyl.

11. A compound or salt as recited in claim 1, wherein R is selected from the group consisting of unsubstituted or substituted D- or L-phenylalanine, unsubstituted or substituted D- or L-2-naphthyl alanine, unsubstituted or substituted D- or L-2-thienyl alanine, unsubstituted or substituted D- or L-3-fluorophenyl alanine, and unsubstituted or substituted D- or L-3-pyridyl alanine.

12. A compound or salt as recited in claim 1, wherein each said halogen atom independently is selected from the group consisting of fluorine, chlorine, bromine and iodine atoms.

13. A pharmaceutical composition comprising a compound or salt as recited in claim 1 and a pharmaceutically acceptable carrier.

14. A salt as recited in claim 1, wherein said salt is selected from the group consisting of salts of sodium, potassium, magnesium, calcium, hydrogen chloride, tartaric acid, succinic acid, fumaric acid and p-toluenesulfpnic acid.

15. A compound selected from the group consisting of:
- (5S,6R)-6-(2S-2-benzyloxycarbonylamino-2-phenylmethyl-acetamido)-4-thia-1-azabicyclo [3,2,0] heptan-7-one;
- (5S,6R)-6-(2S-2-benzyloxycarbonylamino-2-phenylmethyl-acetamido)-4,4-dioxo4-thia-1-azabicyclo [3,2,0] heptan-7-one;
- (5R,6R)-6-(2S-2-benzyloxycarbonylamino-2-phenylmethyl-acetamido)-4,4-dioxo-4-thia-1-azabicyclo [3,2,0] heptan-7-one;
- (5S,6R)-6-{2S-2-(3-phenylpropionoyl)amino-2-cyclohexylmethyl-acetamido}- 4-thia-1-azabicyclo [3,2,0] heptan-7-one;
- (5S,6R)-6-{2S-2-(3-phenylpropionoyl)amino-2-cyclohexylmethyl-acetamido}-4,4-dioxo-4-thia-1-azabicyclo [3,2,0] heptan 7-one;
- (5S,6R)-6-{2S-2-(3-phenylpropionoyl)amino-2-(2-naphthyl)methyl-acetamido}-4-thia-1-azabicyclo [3,2,0] heptan-7-one;
- (5S,6R)-6-{2S-2-(3-phenylpropionoyl)amino-2-(2-naphthyl)methyl-acetamido}-4,4-dioxo-4-thia-1-azabicyclo [3,2,0] heptan-7-one;
- (5S,6R)-6-{2S-2-(3-phenylpropionoyl)amino-2-(2-thienyl)methyl-acetamido}-4-thia-1-azabicyclo [3,2,0] heptan-7-one;
- (5S,6R)-6-{2S-2-(3-phenylpropionoyl)amino-2-(2-thienyl)methyl-acetamido}-4,4-dioxo-4-thia-1-azabicyclo [3,2,0] heptan-7-one;
- (5S,6R)-6-{2S-2-(3-phenylpropionoyl)amino-2-(3-fluorophenyl)methyl-acetamido}-4-thia-1-azabicyclo [3,2,0] heptan-7-one;
- (5S,6R)-6-{2S-2-(3-phenylpropionoyl)amino-2-(3-fluorophenyl)methyl-acetamido}4,4-dioxo-4-thia-1-azabicyclo [3,2,0] heptan-7-one;
- (5S,6R)-6-{2S-2-benzyloxycarbonylamino-2-(3-pyridyl)methyl-acetamido}-4-thia-1-azabicyclo [3,2,0] heptan-7-one;
- (5S,6R)-6-{2S-2-benzyloxycarbonylamino-2-(3-pyridyl)methyl-acetamido}-4,4-dioxo-4-thia-1-azabicyclo [3,2,0] heptan-7-one;
- (5S,6R)-6{2R-2-benzyloxycarbonylamino-2-phenylmethyl-acetamido}-4,4-dioxo-4-thia-1-azabicyclo[3,2,0] heptan-7-one; and
- (5S,6R)-6-{2S-2-benzyloxycarbonylamino-2-phenylmethyl-acetamido}-4-oxo-4-thia-1-azabicyclo [3,2,0] heptan-7-one.

16. A compound or salt as recited in claim 1, wherein n=1 or 2.

* * * * *